(12) United States Patent
Goldstein et al.

(10) Patent No.: US 6,720,191 B1
(45) Date of Patent: Apr. 13, 2004

(54) MECHANICAL HANDLING SYSTEMS FOR LASER CAPTURE MICRODISSECTION

(75) Inventors: Seth R. Goldstein, Bethesda, MD (US); Robert F. Bonner, Washington, DC (US); Paul D. Smith, Annapolis, MD (US); John Peterson, Falls Church, VA (US); Thomas Pohida, Monrovia, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/601,559

(22) PCT Filed: Jan. 29, 1999

(86) PCT No.: PCT/US99/01987

§ 371 (c)(1),
(2), (4) Date: Oct. 30, 2000

(87) PCT Pub. No.: WO99/39176

PCT Pub. Date: Aug. 5, 1999

Related U.S. Application Data
(60) Provisional application No. 60/073,480, filed on Feb. 3, 1998.

(51) Int. Cl.[7] .......................... G01N 1/00; G01N 33/48; G01N 21/00; C12N 5/02; B32B 27/04

(52) U.S. Cl. .......................... 436/174; 436/43; 436/63; 435/325; 422/50; 422/63; 422/64; 422/65; 422/66; 422/68.1

(58) Field of Search ............... 436/43, 63, 174; 356/36; 422/50, 58, 68.1, 63–66; 435/325

(56) References Cited

U.S. PATENT DOCUMENTS

| | | | |
|---|---|---|---|
| 4,624,915 A | 11/1986 | Schindler | 435/4 |
| 4,629,687 A | 12/1986 | Schindler | 435/4 |
| 5,843,644 A | 12/1998 | Liotta et al. | 435/6 |
| 5,843,657 A | 12/1998 | Liotta et al. | 435/6 |
| 5,981,218 A | 11/1999 | Rio et al. | 435/69.1 |
| 5,985,085 A | 11/1999 | Baer et al. | 156/284 |
| 6,010,888 A | 1/2000 | Liotta et al. | 435/100 |
| 6,100,051 A | 8/2000 | Goldstein et al. | 435/40.5 |
| 6,184,973 B1 * | 2/2001 | Baer et al. | 356/36 |
| 6,531,318 B1 * | 3/2003 | Palmer-Toy et al. | 436/63 |

* cited by examiner

Primary Examiner—Jill Warden
Assistant Examiner—Brian Sines
(74) Attorney, Agent, or Firm—William Michael Hynes; Townsend and Townsend and Crew LLP

(57) ABSTRACT

A method and apparatus of gathering by LCM identified cellular material from random locations on a tissue sample to designated locations on a transporting substrate enables convenient further processing. A transporting substrate has an identified mapped location for receiving identified cellular material. At least a segment of a selectively activatable coating is placed on the side of the transporting substrate in apposition to the tissue sample at the mapped location. The transporting substrate and sample are relatively moved to place the selectively activated coating at the mapped location in apposition to identified cellular material of the tissue sample which is to be extracted. Thereafter, the selectively activatable coating is activated and impressed or impressed and activated to form an adhesive region on the transporting substrate for adhering to the identified cellular material. Upon removal of the transporting substrate from the tissue sample, identified cellular material adheres to the transporting substrate at the mapped location.

10 Claims, 8 Drawing Sheets

MECHANICAL HANDLING SYSTEMS FOR LASER CAPTURE MICRODISSECTION

This application claims benefits of provisional 60/073,480 filed Feb. 3, 1998.

This application claims priority from PCT/US 96/16517 filed Oct. 9, 1996 of Lance A. Liotta, et al. entitled Isolation of Cellular Material Under Microscopic Visualization. This application also claims priority from US Provisional Application, Serial No. 60/036,927, filed Feb. 7, 1997 entitled Isolation of Cellular Material Under Microscopic Visualization. Both of these applications are incorporated herein by reference as if fully set forth.

This invention relates to laser capture microdissection (LCM) in which direct extraction of cellular material from a tissue sample occurs to a transfer surface. The disclosure herein relates to isolating selected tissue samples to a film matrix in a format where the isolated sample segments can be conveniently collected for subsequent analysis.

BACKGROUND OF THE INVENTION

Laser Capture Microdissection (LCM) has been described in Science magazine (Nov. 8, 1996 and Nov. 21, 1997). Summarizing, LCM typically involves placing a transporting substrate having an activatable coating for adhering to identified cellular material on a tissue sample. For example, a large (several cm$^2$) piece of transparent, thermally activatable adhesive film (e.g. EVA polymer) is placed in close apposition with the upper tissue surface of a standard (desiccated) histopathology section (5–15 um thick) mounted on a glass microscope slide.

Once the identified cellular material of the tissue sample for micro-dissection is selected, typically by examination under a microscope, the substrate is then activated, typically be being pulsed with laser beam. The light energy is absorbed by the plastic film which melts in a small region. The activatable coating then flows onto and around microscopic tissue components thereby causing the film on cooling to be firmly adherent to the identified cellular material of tissue sample. Other target areas on the same slide can similarly treated.

When the film is subsequently lifted off the slide, the selected tissue comes with the film in a series of spots leaving the other tissue behind on the slide. Unfortunately, just as the identified cellular material was dispersely located on the slide, the identified cellular material is dispersely distributed on the transporting substrate.

In the ordinary case, the selected series of spots is then removed from the film by placing the film in a suitable reagent (e.g., proteinase K which digests the structural proteins of the tissue) which frees the molecules of DNA or RNA to be subsequently analyzed (using, e.g., PCR and gel electrophoresis). In order to confer specific transfer of single targets to a given reagent solution (i.e., specific "molecular extraction buffers"), the transferred tissue spots and underlying attached film can be manually excised with a scalpel or scissors, or punched out with a precision punch/die directly into a cuvette.

With the development of this technique, demand has arisen for refinement. Accordingly, and in the text that follows, we identify the requirements of LCM and thereafter propose solution to those requirements. It is to be understood that in setting forth the requirements for laser capture microdissection, we claim invention. It goes without saying that the recognition of the problem to be solved can constitute part of the invention along with the solution to the problem once it is recognized.

In LCM, there is potentially a great research need (and eventual clinical need) to transfer smaller and smaller spot sizes (e.g. 25 microns or less). This leads to transfer of selected single cells or even organelles in order to study molecular modifications of specific cells within a pathology or cytology specimen. This poses two technology problems:

1) the accurate targeting, and adhesion of the film to specific cells based on microscopic observation, and
2) keeping the specificity of transfer high by minimizing the adjacent area of film transferred into the molecular extraction buffers.

In LCM, the spots in the film are randomly located roughly in a position corresponding to their location on the sample. When smaller spot sizes of sample are extracted, a problem which arises is finding them on the removed piece of film or transfer surface. Precise location is required so that the extracted portions of the sample can be precisely cut out. With precision cutting, the target tissue is completely recovered with minimal contamination from surrounding areas of film with low density nonspecific tissue adhesion.

Restricting LCM to the disclosed technology, precise computer control of the storage position and storage of coordinates may be practical. However, this computer control may loose the reliability of visual observation of the transfer process and may be complex and expensive. Further, computer location could fail to be accurate in many cases such as when the tape is distorted when it is lifted off the slide.

Nonspecific transfer to the film of un-targeted tissue in the region surrounding the identified cellular material is another problem. This non-specific transfer becomes increasingly important as spot size of targeted tissue is reduced. Ideally, no tissue outside the targeted region illuminated by the laser should be attached to the film upon its removal from the slide. Attachment of any undesired tissue would cause sample contamination with the desired tissue. As smaller and smaller target spots are used, the amount of stray tissue which can be tolerated becomes proportionally smaller.

Presuming that an extremely small contact area with a sample can be achieved, a problem then arises as to how to handle the transfer surface. Specifically, the positioning of a small spot of activatable transfer surface on the tissue at the target site, picking the small activated transfer surface off the tissue, and placing the isolated targeted cells in a cuvette, or storing them in a specifically identifiable manner without contamination by un-targeted tissue elements.

Having set forth the requirements, we now turn attention to a solution.

SUMMARY OF THE INVENTION

A method and apparatus of gathering by LCM identified cellular material from random locations on a tissue sample to designated locations on a transporting substrate enables convenient further processing. A transporting substrate has an identified mapped location for receiving identified cellular material. At least a segment of a selectively activatable coating is placed on the side of the transporting substrate in apposition to the tissue sample at the mapped location. The transporting substrate and sample are relatively moved to place the selectively activated coating at the mapped location in apposition to identified cellular material of the tissue sample which is to be extracted. Thereafter, the selectively activating coating is activated and impressed or impressed and activated to form an adhesive region on the transporting substrate for adhering to the identified cellular material. Upon removal of the transporting substrate from the tissue sample, identified cellular material adheres to the transporting substrate at the mapped location.

In a first embodiment, individual small pieces or coatings of selectively activated material are placed on a transporting film. For example, a selectively activatable coating is placed at the center of discrete pieces of film and exposed toward the sample. Each different piece of film is separately activated at its coated center by the laser. Apposition to the tissue during or after laser action occurs by using a pressure plate.

In an alternate embodiment, a continuous strip including a transparent substrate is used to hold the film, such as a continuous reel of tape with equally spaced, centrally located pieces of selectively activatable coatings. Thereafter, the continuous strip of transparent substrate is incrementally advanced so that center of the activatable coating is in the center of the microscope field. Adjacent bar codes or other optical encoded identifiers could serve to identify the individual transferred samples.

Sample collection can include a pressure plate actuated to hold the transporting substrate in contact with the tissue in the center of the microscope field before or after laser heating. After laser heating and attachment to the selected material from the sample, the pressure plate is raised, and the transporting substrate with the local activated coating with adherent tissue separated from the tissue sample. This process is sequentially repeated so that the transporting substrate is again advanced, the next piece of transporting substrate (clean) is put into the center of the field, pressed onto the tissue surface, and laser activated. This repetition not only advances the transporting substrate but also applies forces to reproducibly lift the targeted (adherent) tissue off the specimen slide. After the transporting substrate is advanced to the next clean (unused) spot, but before the film is pressed onto the specimen surface, the microscope stage and transporting substrate will be translated (in x & y) so that the next tissue target is in the center of the microscope field.

Where the transporting substrate is utilized with selectively coated spots, the substrate can be locally removed from the remainder substrate tape by punching or cutting off or peeling off the local regions of activated coating. This will leave attached identified cellular material localized to small pieces of transporting substrate. These small pieces of transporting substrate can be placed into a specific chamber or vessel for further processing and molecular analysis.

In another embodiment, the individual pieces of selectively activatable coating are mounted at the ends of arrays of deflectable struts attached to and projecting from a central common support, such as a wheel or a comb like structure. Each strut with its selectively activatable coating at the end acts as the transporting substrate and is sequentially indexed through the center of the microscope field. The ends of the struts serve as pressure plates, contacting the tissue with the activatable coating at the ends of the struts. The selectively activatable coat can be actuated when the strut is deflected, e.g., by a solenoid, (one spoke at a time, similar to a daisy wheel printer). After activation, the force on the strut is removed, allowing the strut to lift off the slide with the identified cellular material adhered to it. Thereafter, the strut array indexes the next strut with its piece of film into place, the stage can be moved to the next tissue target and the next strut is placed in contact with the new target.

Another variant of this approach is to use a comb shaped array (i.e, target film spots are in a linear array attached to a linear carriage by parallel spokes perpendicular to the array axis rather than the radial spokes of a "daisy wheel"). A minute spot of film is placed at the end of each comb finger. A small solenoid deflects the finger so its end, which acts as a pressure plate, contacts the tissue in the center of the field. After laser heating, the solenoid force is removed, the finger returns to its undeflected position (lifting off the slide the tissue adhered to the film), and the comb is linearly indexed so a different finger/piece of film is in the center of the field and a different tissue target can be moved in place. Marks on the base of the comb could identify the samples. This technique allows extremely small and precise sample extraction.

Where the adhesive film is bonded to a pressure plate in the form of a deflectable strut, the strut at the attached identified cellular material can be broken off, and this broken off portion deposited into a capsule for collection and further processing.

It should be understood that in all the above collection techniques, other means exist to detach the adhesive spot from the substrate (e.g, pull tabs and peeling; specific solvents for the bond between the substrate and the adhesive spot, etc). All these improvements provide a means of removing precisely spaced (linear or angular separation) target film spots of small size which can easily be precisely positioned on the center of the optical field at a target site of the specimen already translated to this position under microscopic observation. Since the samples can be provided with identifying marks on the adjacent substrate, they can be stored in a compact manner as an array of sequential transfers (a daisy wheel, comb, or strip of tape substrate) until individually separated or grouped according to cell type from among a series of transfers and removed from their substrates.

In yet another embodiment, a piece of continuous transporting substrate is provided with a continuous central and narrow selectively activatable coating. This piece of continuous film is put in contact with the tissue at the narrow selectively activatable coating by a narrow (in the direction of the film travel) pressure plate to define the (small) area of contact. This technique avoids the problem of aligning, in the direction of film travel, a discrete spot of adhesive with the center of the field. As long as the narrow adhesive part of the tape passes through the field, and the stationary pressure plate is lined up with the field—both modest requirements—alignment will be satisfactory. This approach has the advantage that it enables a small contact area of adhesive film on the tissue without: a) complications due to handling and alignment between the film and the target area, b) requiring specialized developments in the film above and beyond its basic adhesive properties, and c) requiring development of a specialized tape cassette e.g. with a built in pressure plate etc.

BRIEF DESCRIPTION OF THE DRAWINGS

FIG. 2A–2E are a side elevation cartoon series of the sequential removal of selected sample from a slide mounted specimen in which:

FIG. 2A is illustrates the transporting film with coating attached to a selected specimen at a slide with the pressure plate withdrawn from contact with the slide;

FIG. 2B illustrates the apparatus of FIG. 2A with the tape being advanced to withdraw the selected portion of the sample from the slide;

FIG. 2C illustrates the tape completely advanced for receipt of the next sequential sample;

FIG. 2D illustrates the tape clamped as advance prior to collection of the next sample section;

FIG. 2E illustrates the pressure plate pushing the activatable coating against the next sequentially selected portion of the sample;

FIG. 14A shows the selectively activated coating on one side of the transporting substrate recessed from the target tissue by a gap;

FIG. 14B illustrates schematically laser energy being directed through the tissue sample to the selectively activated coating to activate that coating and cause the activated coating to expand downward to the sample at the identified cellular material;

FIG. 14C illustrates the transporting substrate and selectively activated coating after adhesion of the cellular material and contraction of the selectively activated coating to the transporting substrate;

FIG. 14D illustrates the transporting substrate of FIG. 14C with a new and different slide and tissue sample placed under the substrate; and, FIG. 14E illustrates the transporting substrate having samples from two differing slides, the collection here illustrated showing an effective concentration selected cellular material, even though the selected material was contained on two separate samples.

DESCRIPTION OF THE PREFERRED EMBODIMENT

Figure 1:
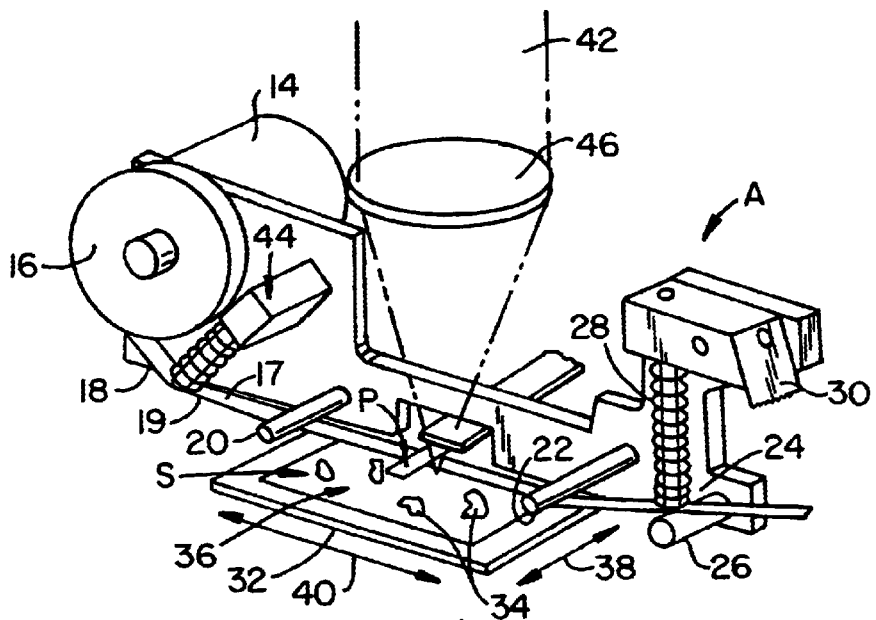
FIG. 1 is a perspective view of a mechanism for the practice of LCM including a supply reel, a laser activation system, a pressure plate for pushing the activated coating against a sample, and a cutting mechanism for generating discrete film sections with selected portions of the specimen contained thereon.

Referring to FIG. 1, film strip laser capture microdissection apparatus A is illustrated. Stepper motor 14 drives supply reel 16 dispensing coated tape 18. Coated tape 18 passes over first guide bar 20, second guide bar 22 to tape stop mechanism 24. Tape stop mechanism 24 includes stop bar 26 bearing on coated tape 18 from below (the side to which sample S) is ultimately collected and solenoid actuated tape stop plunger 28. Tape cut off knife 30 enables tape with contained sample S to be cut into small strips for further processing.

Slide 32 contains sample S, which sample includes desired sample sections 34 mixed irregularly with tissue 36 of sample S. It is the purpose of this disclosure to isolate with precision desired sample sections 34 from sample S.

In order from such isolation to occur, visualization of sample S must occur. As here illustrated, microscope M having an inverted optical path looking up from under slide 32 is shown schematically by eye E. As is conventional, slide 32 is mounted to a stage which is transportable in x-direction 38 and y-direction 40.

Finally, and once sample S at desired sample sections 34 is centered within a viewing field, it is necessary to gather desired sample sections 34 of sample S to coated tape 18. In such gathering, coated tape 18 is activated by laser light source 42. After or during such activation, the activated coating on coated tape 18 is contacted to sample S at desired sample sections 34. This contacting or juxtaposition between coated tape 18 and desired sample sections 34 occurs by pressure plate P bearing down on uncoated side 17 of coated tape 18 to cause the tape to move into apposition with sample S at desired sample sections 34. Adhesion of desired sample sections 34 occurs to coated side 19 of coated tape 18.

It may be desirable to maintain constant tension between supply reel 16 on dispensed coated tape 18. Accordingly, there is provided tape tensioning apparatus 44. It will be understood that this apparatus is optional.

Once coated tape 18 has adhered to desired sample sections 34, the tape is moved. Under the normal circumstance, the tape will have sufficient adhesion to desired sample sections 34 to dissect the sample section from the remainder of the tissue of sample S.

Figure 2A:
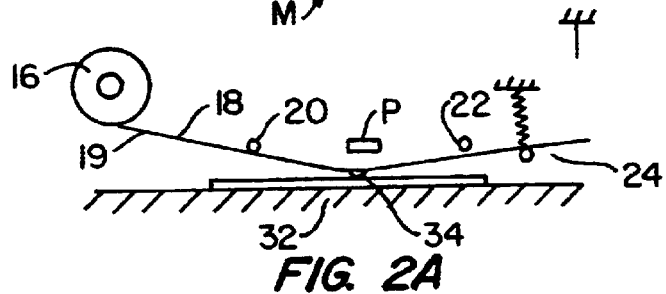
Figure 2B:
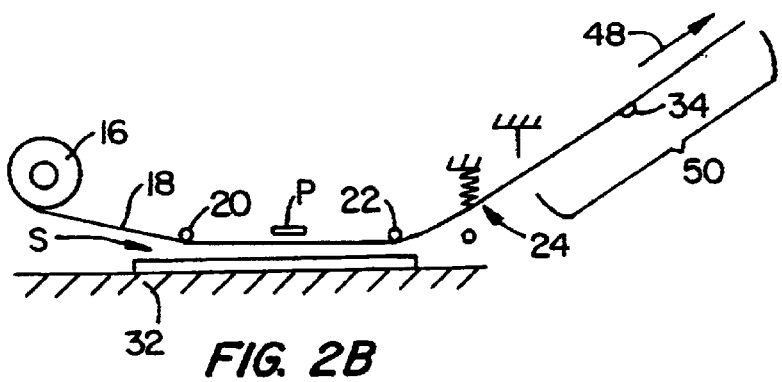
Figure 2C:
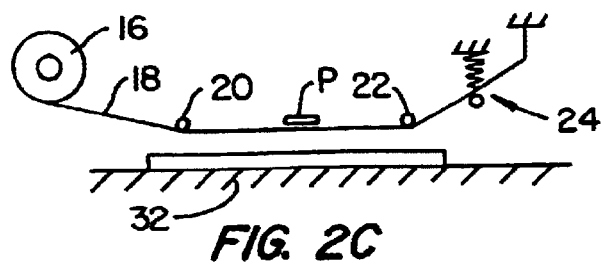
Figure 2D:
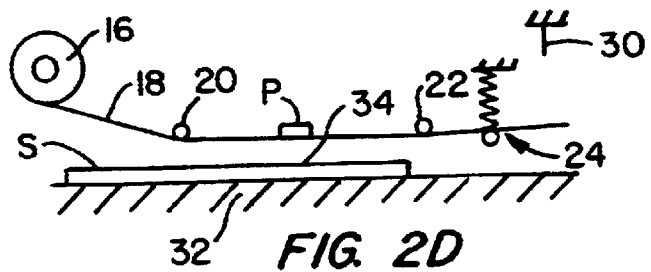
Figure 2E:
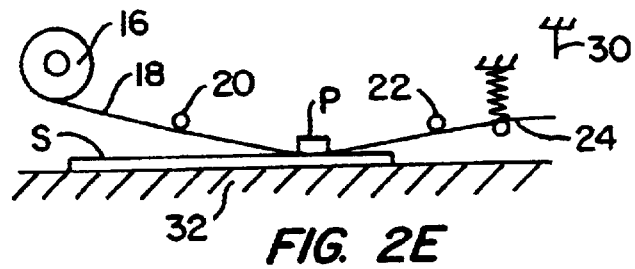
Figure 2F:
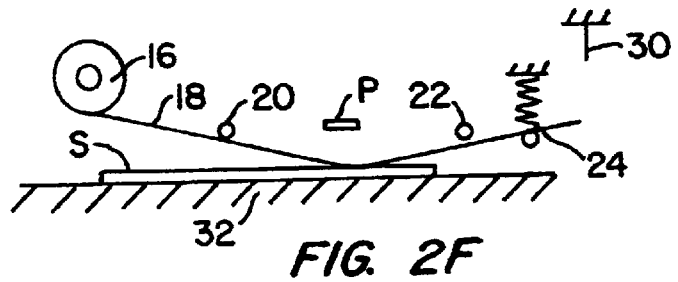
FIG. 2F illustrates the cycle ready for repeat; it being seen that FIG. 2F illustrates the same cycle state as that previous observed in FIG. 2A.

Referring to FIGS. 2A–2F, a schematic cartoon series of this apparatus is illustrated. In FIG. 2A, supply reel 16 is shown having coated tape 18 with coated side 19 in contact with sample S on slide 32. Because of previous activation, coated tape 18 is now adhered to desired sample sections 34 of sample S. As can be seen in the view of FIGS. 2A and 2F, pressure plate P is withdrawn.

Referring to FIG. 2B, force 48 pulling tape 18 around guide 22 has lifted sample section 34 off the slide and made the uncoated side of the tape 17 deflect the plunger 28 allowing the coated side of the tape 18 and the sample 34 to avoid touching the stop bar 26 as it moves sample 34 out from under P, and draws the tape away from the supply reel 16. Stepper motor 14 causes a measured amount of coated tape 18 to be withdrawn from supply reel 16. When the limit of this measured amount is reached, stepper motor 14 freezes, and coated tape 18 is ready to be cut by tape cut off knife 30. Naturally, with stepper motor 14 precisely controlling dispensing of coated tape 18, the placement of desired sample sections 34 relative to the overall length cut off at tape cut off knife 30 occurs.

Thus, it will be seen that the transporting substrate has an identified mapped location for receiving identified cellular material.

In FIG. 2C, tape segment 50 has been cut and removed. Further, tape stop mechanism 24 has been activated. As a consequence, the end of coated tape 18 is a fixed distance from P and is disposed for the collection of the next visualized sample when pressure plate P deflects the tape onto the slide.

Referring to FIG. 2D, it will be seen that slide 32 and consequently sample S have been moved to a new position. In this new position, another desired sample section 34 has been centered for pick up by movement of slide 32 in x-direction 38 and y-direction 40.

Finally, and with respect to FIG. 2E, pressure plate P causes juxtaposition of coated tape 18 at coated side 19. Stepper motor 14 is no longer frozen in order to provide the amount of slack necessary to deflect the tape onto slide 32. Again activation of coated side 19 by laser light source 42 through laser light focusing lens 46 occurs.

Referring to FIG. 2F, the cycle illustrated is ready for repeat; it being seen that FIG. 2F illustrates the same cycle state as that previous observed in FIG. 2A.

In considering the operation of FIGS. 2A–2E, it can be seen that at least a segment of a selectively activated coating is placed on the side of the transporting substrate in apposition to the tissue sample what amounts to a mapped location. Further, and during the gathering of desired sample sections 34, the transporting substrate and sample are relatively moved to place the selectively activated coating at the mapped location in apposition to identified cellular material of the tissue sample which is to be extracted. Thereafter, the selectively activating coating is activated and impressed or impressed and activated to form an adhesive region on the transporting substrate for adhering to the identified cellular material. Upon removal of the transporting substrate from the tissue sample, identified cellular material adheres the transporting substrate at the mapped location.

Figure 4:
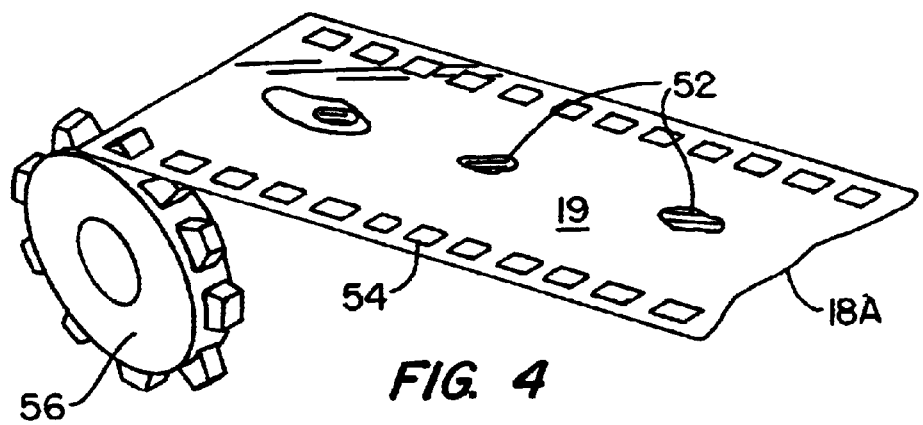
FIG. 4 is a plan view of a first embodiment of transporting tape utilized with this invention in which the film from the supply reel includes separate and discrete evenly spaced spots of selectively activatable coatings for the collection of sample.

It will be understood that coated tape 18 may have several differing configurations. Referring to FIG. 4, coated tape 18A is shown constructed from, e.g., polyester films such as Mylar® having discrete and spaced apart coated spots 52 placed on coated side 19 of the tape. Additionally, sprocket holes 54 are shown for positioning the tape with precision in combination with sprocket 56. Each different discrete and spaced apart coated spots 52 is separately activated at its coated center by the laser. Apposition to the tissue during or after laser action occurs by using a pressure plate.

Figure 5:
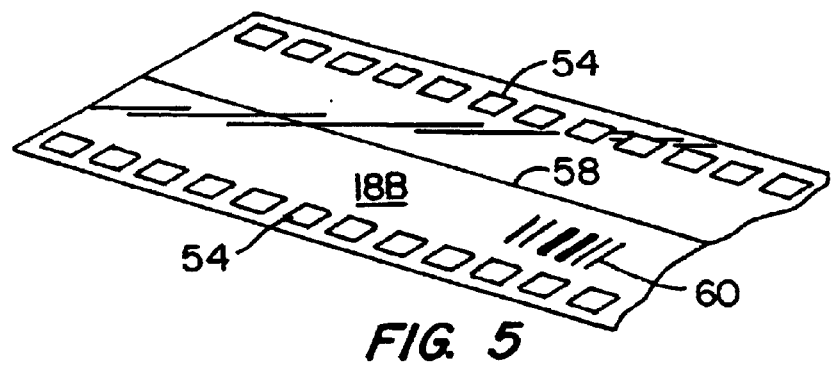
FIG. 5 is a plan view of a second embodiment of the transporting tape here utilizing a separate central strip of selectively activatable coating for impression to the sample.

Referring to FIG. 5, a continuous strip including a transparent substrate is used to hold the film. The continuous strip of transparent substrate or coated tape 18B has continuous central strip of activatable coating 58. Adjacent bar codes 60 or other optical encoded identifiers could serve to identify the individual transferred samples, which samples can be either anywhere along the continuous central strip of activatable coating 58 or evenly spaced.

Figure 11:
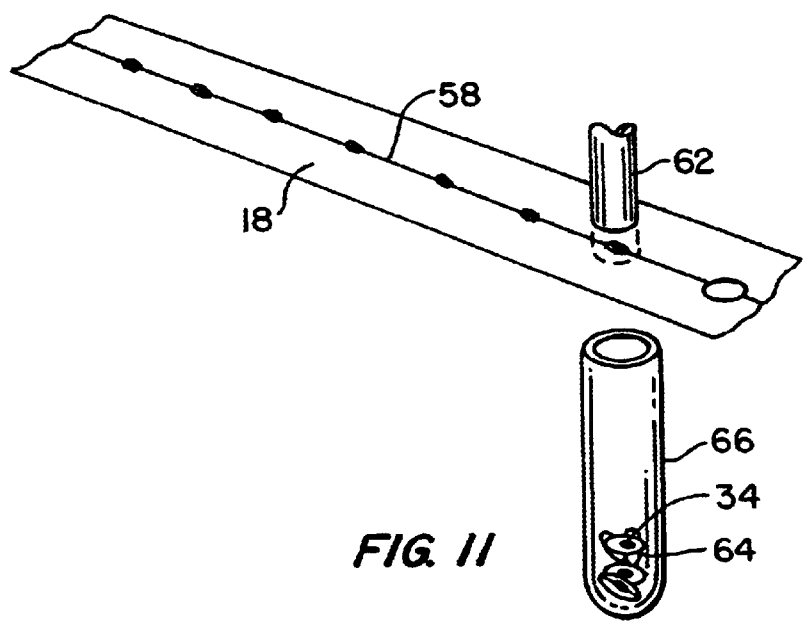
FIG. 11 illustrates sample being extracted from a tape to a collection vial.

Referring to FIG. 11, it will be understood that where coated tape 18 is utilized, transporting substrate with selectively coated spots or discrete and spaced apart coated spots 52 likewise can be used. The substrate can be locally removed from the remainder of the substrate tape by punching or cutting off the local regions of activated coating.

Referring to FIG. 11, punch 62 is shown separating desired sample sections 34 on punched film sections 64. This will leave attached identified cellular material or desired sample sections 34 localized to small pieces of transporting substrate on punched film sections 64. These small pieces of transporting substrate can be placed into a specific chamber or vessel such as test tube 66 for further processing and molecular analysis.

Figure 6:
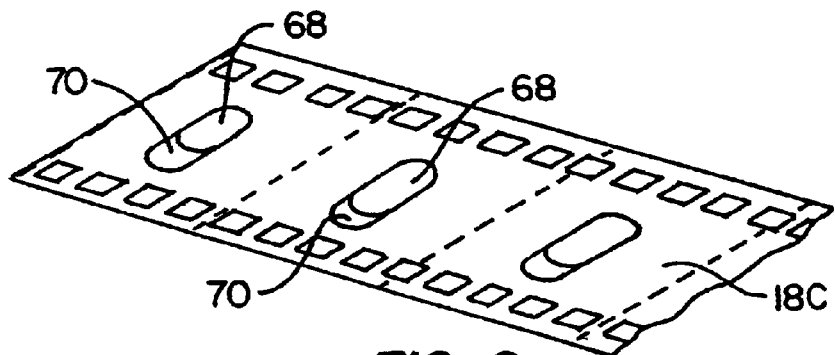
FIG. 6 is a plan view of a tape having detachable sections with activatable coatings on the detachable sections.

Referring to FIG. 6, an additional embodiment is illustrated. In this case, activatable coating 68 is attached to pull tabs 70 on coated tape 18C. As is apparent, by removal of pull tabs 70, sample gathered to activatable coating 68 is likewise removed.

Figure 7:
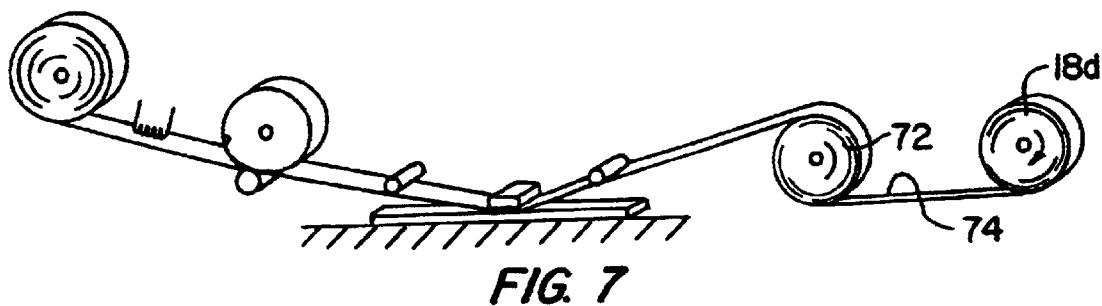
FIG. 7 is a side elevation perspective illustrating a tape having a covering layer and illustrating the placement of marker coding on either the transporting substrate or the covering layer for subsequent retrieval of the tape.
Figure 3:
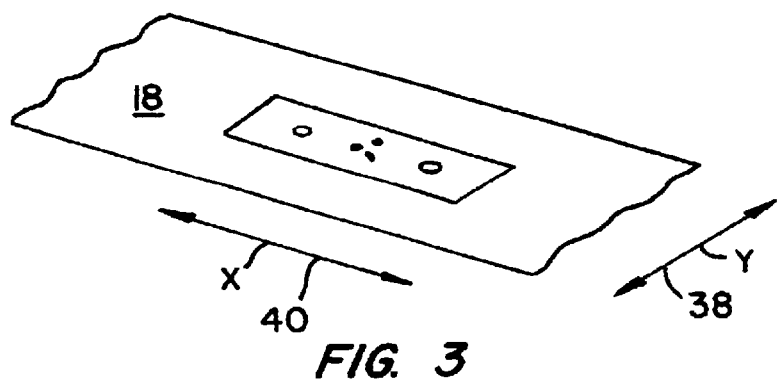
FIG. 3 is a schematic of tape being disposed parallel to the elongate axis of an underlying side with the pressure plate having transverse excursion relative to the slide to enable X and Y excursion of the sample collection point of the apparatus.

It should be understood that there may be a need to collect and thereafter store sample connected to tape. Accordingly, and referring to FIG. 7, coated tape 18D is shown being gathered to take up roll 72. At the same time, covering tape 74 covers over and helps in the preservation of the remaining sample on an interleave basis. Sample thus collected can be preserved.

Figure 8:
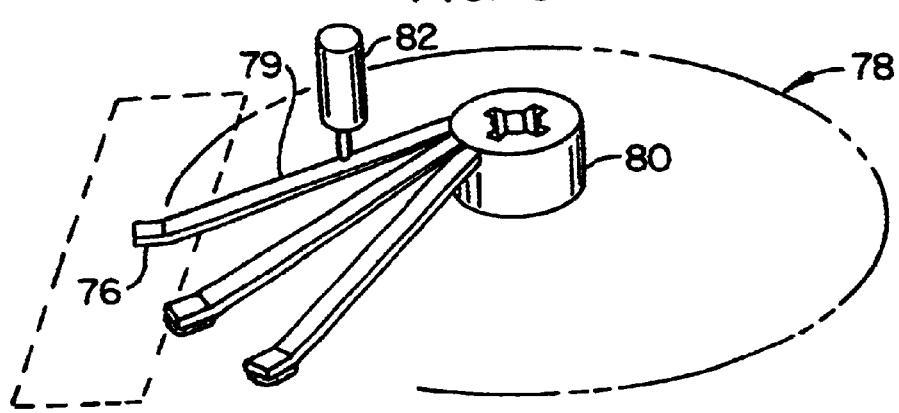
FIG. 8 is a perspective view of a circular spoke apparatus having pads with selectively activatable coatings for the collection of selected sample from a specimen.

Referring to FIG. 8, another embodiment of this invention is set forth. Individual pieces of selectively activatable coating 76 are mounted at the ends of spoke arrays 78 attached to and projecting from central common support, such as central hub 80. Spoke actuator 82 selectively depresses each spoke 79 of spoke array 78. As shown in FIG. 8, each spoke with its selectively activatable coating at the end acts as the transporting substrate and is sequentially indexed through the center of the microscope field from central hub 80. The ends of the spokes serve as a pressure plates, contacting the tissue with the activatable coating at the ends of the spokes. The selectively activatable coat can be actuated when the spoke is deflected, e.g., by a solenoid, (one spoke at a time, similar to a daisy wheel printer). After activation, the force on the spoke is removed and the spoke indexed, allowing the spoke to lift off the slide with the identified cellular material adhered to the spoke. Thereafter, the spoke array indexes the next piece of film into place and the stage can be moved to the next tissue target.

In FIG. 8, central hub 80 is utilized. Just as well a comb like structure, or a flexible backing can be used for the substrate support.

Figure 9:
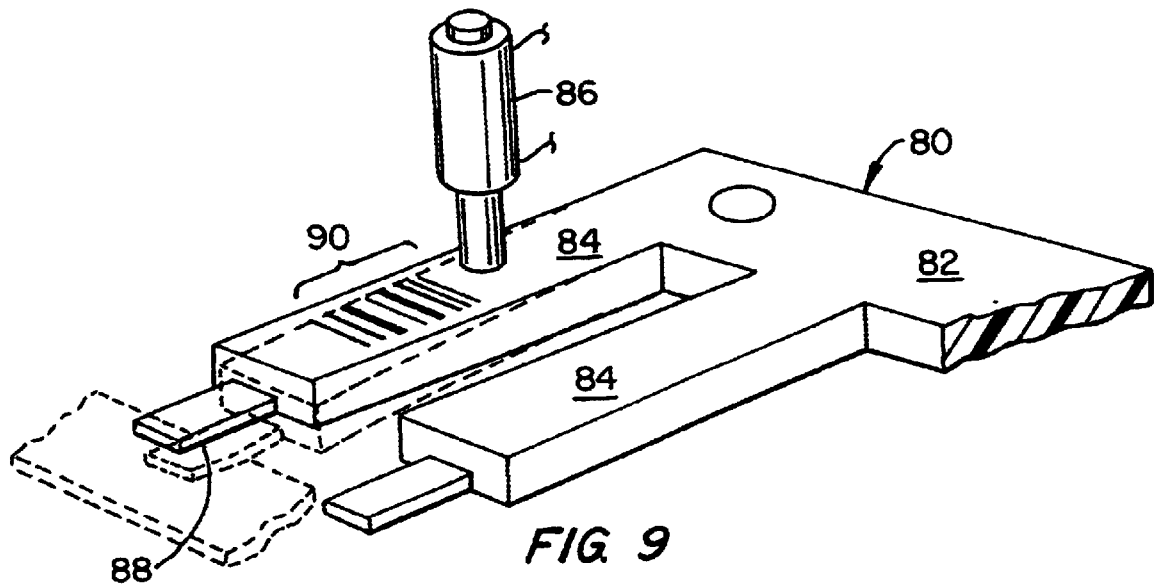
FIG. 9 is a perspective view of a linear spoke array of tines having an overall comb like configuration in which sample is collected by individually actuating successive comb tines to collect designated sample.

Referring to FIG. 9, a preferred variant of this approach is to use comb shaped array 80 (i.e, target film spots are in a linear array attached to a linear carriage by parallel spokes perpendicular to the array axis rather than the radial spokes of a "daisy wheel"). Minute spot of activatable coating 88 is placed a on the undersurface at the end of each comb finger 84. Small solenoid 86 deflects the finger so its end, which acts as a pressure plate, contacts the tissue in sample S in the center of the field.

After laser heating, the solenoid force is removed, the finger returns to its undeflected position (lifting off the slide the tissue adhered to the film), and the comb is linearly indexed so a different finger/piece of film is in the center of the field and a different tissue target can be moved in place. Optical marks 90 on the base of the comb could identify the samples. This technique would allows extremely small and precise sample extraction.

Figure 10:
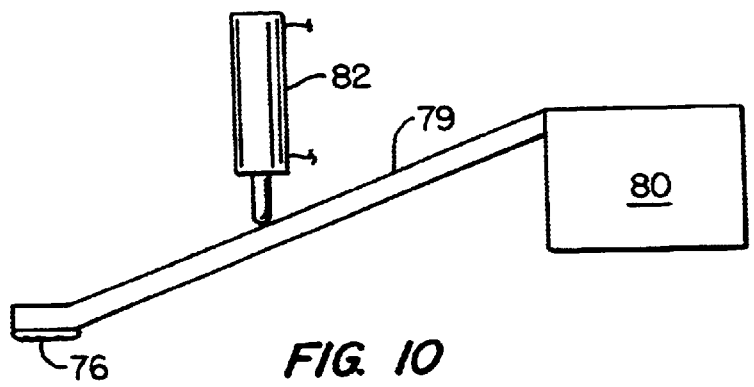
FIG. 10 is a detail at a spoke with the spoke acting through a transporting substrate to impress an activatable coating onto tissue sample with the activatable coating placed at the end of the spoke.
Figure 12:
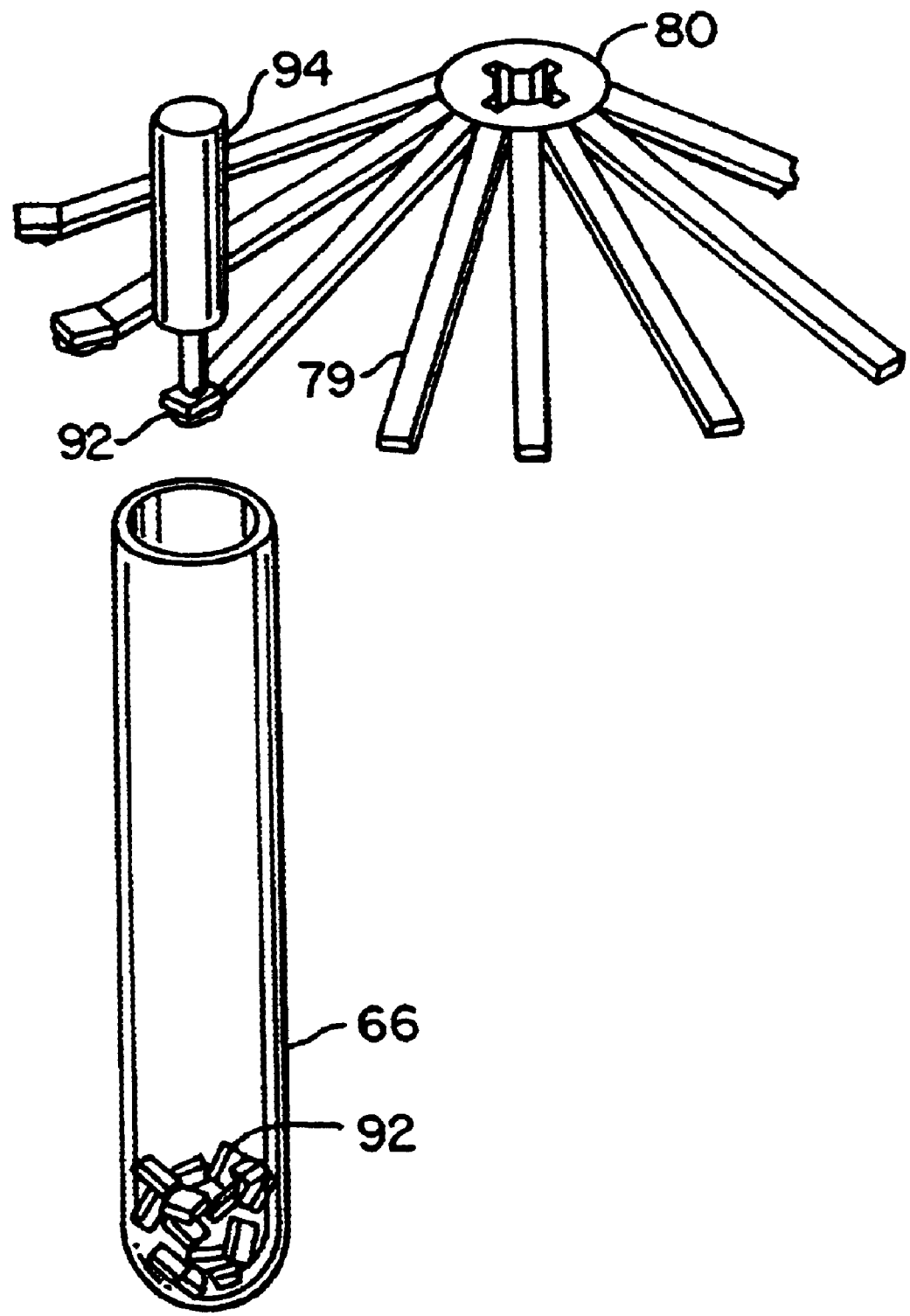
FIG. 12 illustrates sample being collected from a spoke to a collection vial.

Referring to FIGS. 10 and 12, where the adhesive film is bonded to a pressure plate in the form of a spoke, spoke 79 with the attached identified cellular material can be broken off, and the broken off spoke portion 92 deposited into a container such as test tube 66 capsule for collection and further processing. Braking off can occur through breaker solenoid 94 at some convenient point along its length.

Figure 13A:
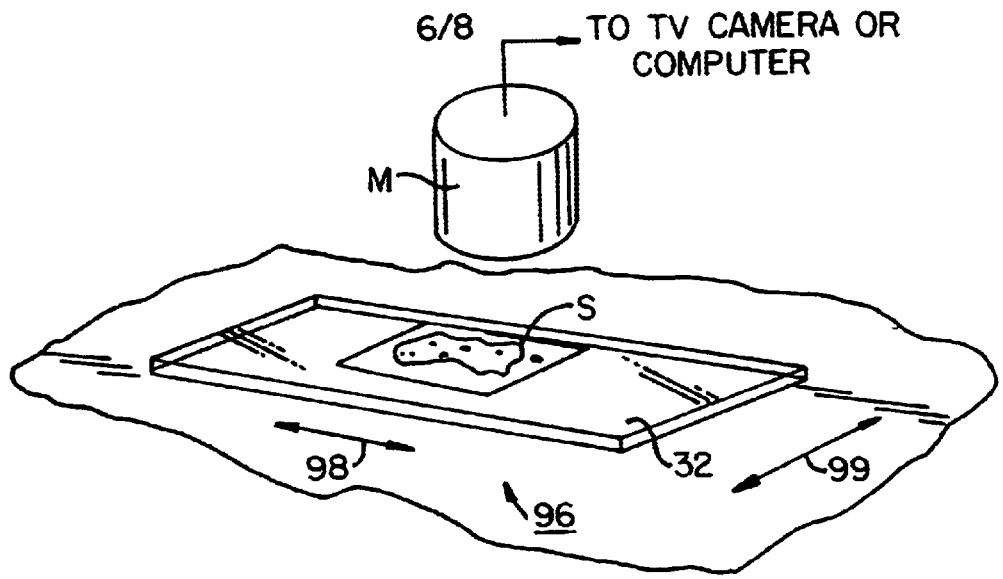
FIG. 13A illustrates an apparatus in which a sample is visualized with the results of visualization being placed into memory.

It is possible with the disclosed invention and known technology to separate visualization and the requisite laser capture micro dissection. Referring to FIG. 13A, slide 32 is shown having sample S viewed by microscope M. Slide 32 is mounted on stage 96 indicated by x-translation arrow 98 and y-translation arrow 99.

Figure 13B:
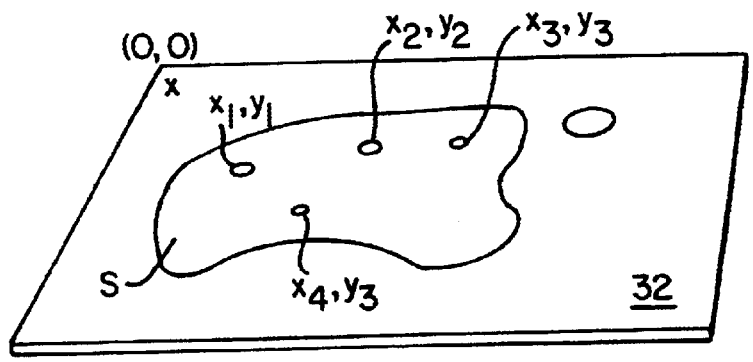
FIG. 13B illustrates the slide of FIG. 13A with schematically indicated selected cellular material locations.

Referring to FIG. 13B, it can be understood that the typical sample S will include number sample locations as schematically indicated by $x_1,y_1$ through $x_4,y_4$. These stage positions, when noted under observation, would be placed in conventional computer memory commonly provided with such stages.

Figure 13C:
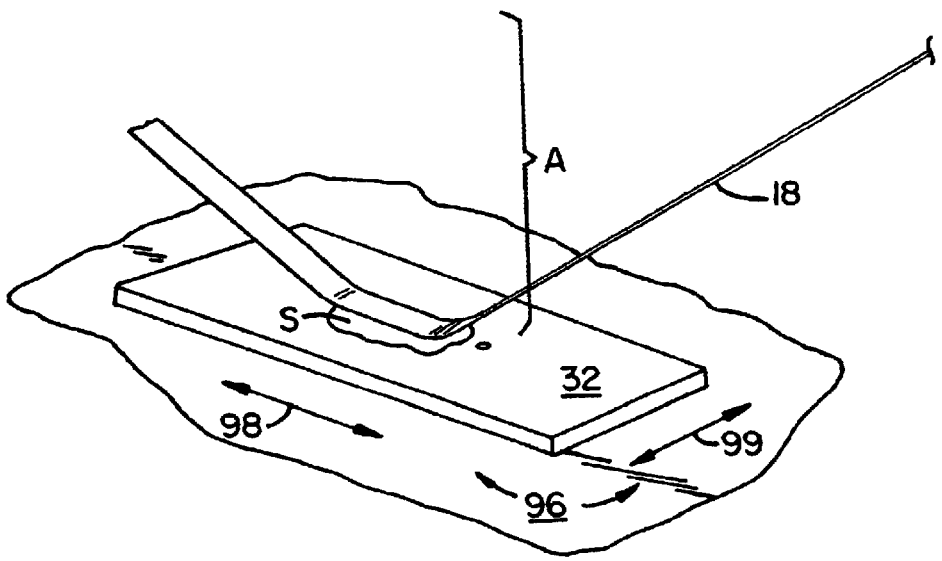
FIG. 13C illustrates the slide of FIG. 13A transferred to apparatus activated to remotely undertake laser capture micro dissection utilizing the memory prepared by the apparatus of FIG. 13A.

Referring to FIG. 13C, it will be seen that laser capture micro dissection is then remote. Specifically, the apparatus of FIG. 2, schematically shown by film strip laser capture micro-dissection apparatus A is shown in the process of sequential gathering of samples at $x_1,y_1$ through $x_4,y_4$ (See FIG. 13B).

It will be understood that with the further progression of modern bioscience, the collection sample can extend to smaller samples. For example, utilizing techniques of laser capture microdissection, it has been possible to collect samples down to a single cell in size (about five (5) microns reduced down to one (1) micron) or subcellular targets. With such small samples, correspondingly reduced analysis volume is required. Furthermore, reagents for some analyses are extremely expensive; the smaller the sample and reagent used, the more economical the test. Laser capture micro dissection is especially adaptable to such circumstances.

Intrinsically, the laser activation allows targeting of elements on a complex tissue slide down to optical diffraction limits (ie. approximately 1 micron). Further, by precise positioning of film and substrate after each transfer, multiple small tissue elements can be precisely concentrated so that they comprise enough homogenous material to allow accurate subsequent processing (such as molecular analysis)

The reader will note that concentration works best where contact between the sample and the tape does not occur before activation. Presuming that precise and accurate tracking of previously accumulated material is made, sample previously collected to the tape will not be physically impacted by sample currently being collected. At the same time, this subsequently collected sample will be adjacent the previously collected sample. By repeating this collection to adjacent portions of a substrate, concentration of the particular cells to be analyzed can occur, even though such cells were not naturally concentrated in situ.

Understanding this much, it is preferred that selected cellular areas should not overlap. If overlapping occurs, sample can be lost. Further, with imprecise collection, the gap utilized could change effecting the predictability of the collection parameters. For example, the dosimetry of the laser radiation could be changed.

As the concept of laser capture micro dissection has developed, precise targeting of ever smaller samples has been required. Surprisingly, it has been discovered that by directing laser energy onto coated tape 18 spaced at some small distance from sample S (about 5 microns or less), very accurate sample collection can occur.

Two comments about this capture can be made. First, the spacing between the tape and sample can be in the broad range of 2 to 20 microns, in the intermediate range of 5 to 15 microns, and preferably about 10 microns when the thickness of the activatable coating is in the preferable range of 100 microns. Thicknesses of the activatable film in the range from 20 to 200 microns can be used. As a practical limit, the thickness should be sufficient that the coating when activated has the desired adhesive effect. As a practical limit, it is presently believed that the coating should exceed 10 microns.

Figure 14A:
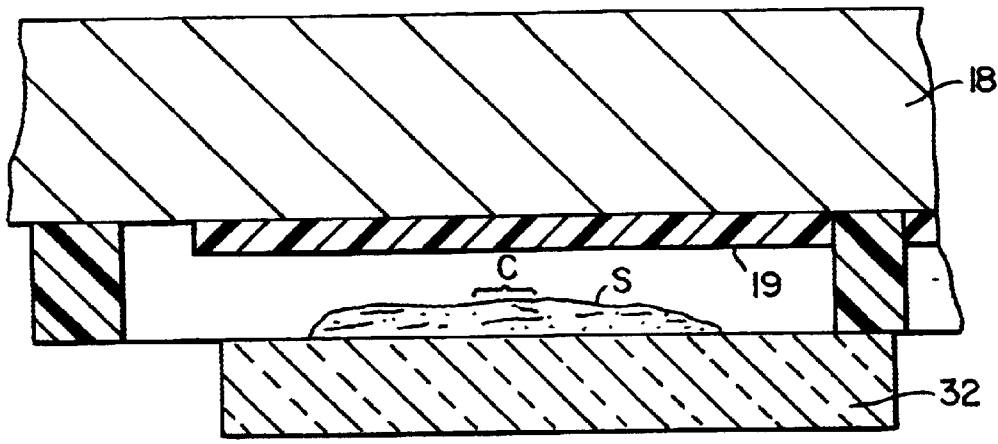
FIGS. 14A–14E are an illustration of activation of the coating in non-contact laser capture microdissection.

Referring to FIG. 14A, slide 32 is shown with sample S. Selected cellular material C has been previously visualized. Overlying slide 32 and sample S, coated tape 18 with coated side 19 addressed downward to the sample is shown.

Figure 14B:
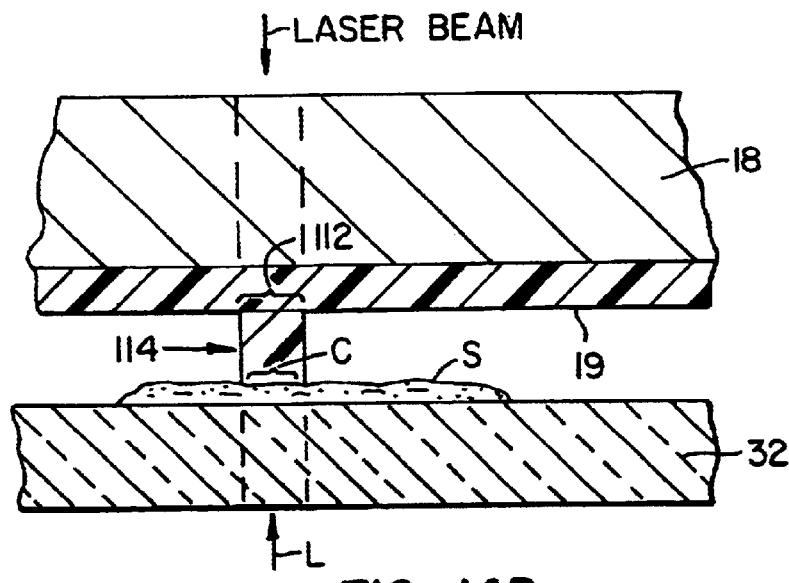

Further, small and accurately focused laser activation of coated tape 18 at coated side 19 occurs through slide 32 and sample S onto coated side 19. Accordingly, referring to FIG. 14B, laser light source L is shown passing through slide 32, sample S, and onto coated side 19. As schematically shown by the broken lines of FIG. 14B, it will be understood that the laser light source L can be incident from an opposite direction.

Coated side 19 becomes locally activated and swells in dimension. Activated region 112 extends downward at extended column 114 and at sample exposed portion 116, fastens to selected cellular material C.

Figure 14C:
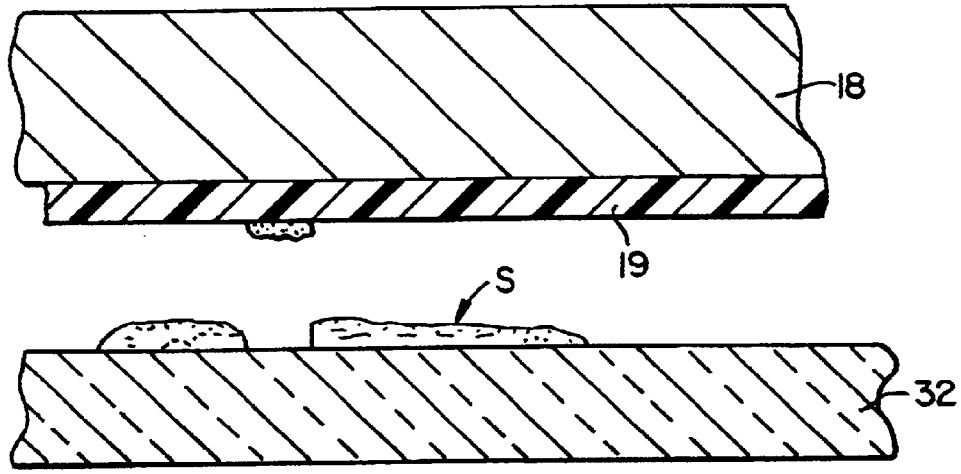

Subsequent to the laser light source L being extinguished, when the activated surface and targeted tissue are removed with the tape from the untargeted region, extended column 114 shrinks, substantially back to the original profile of coated side 19. At this time, the contracting extended column 114 with selected cellular material C separates from sample S. (See FIG. 14C.).

Figure 14D:
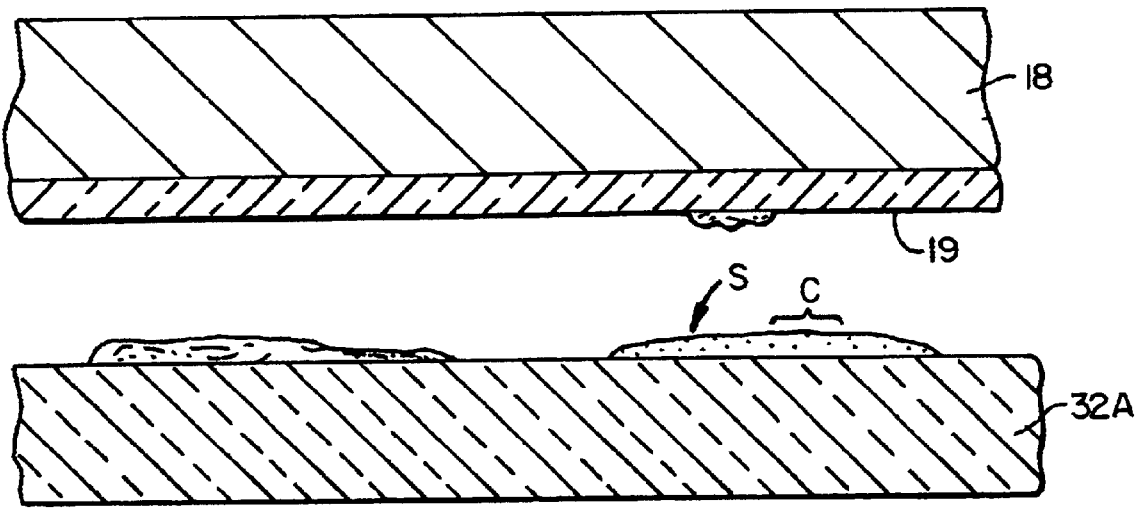
Figure 14E:
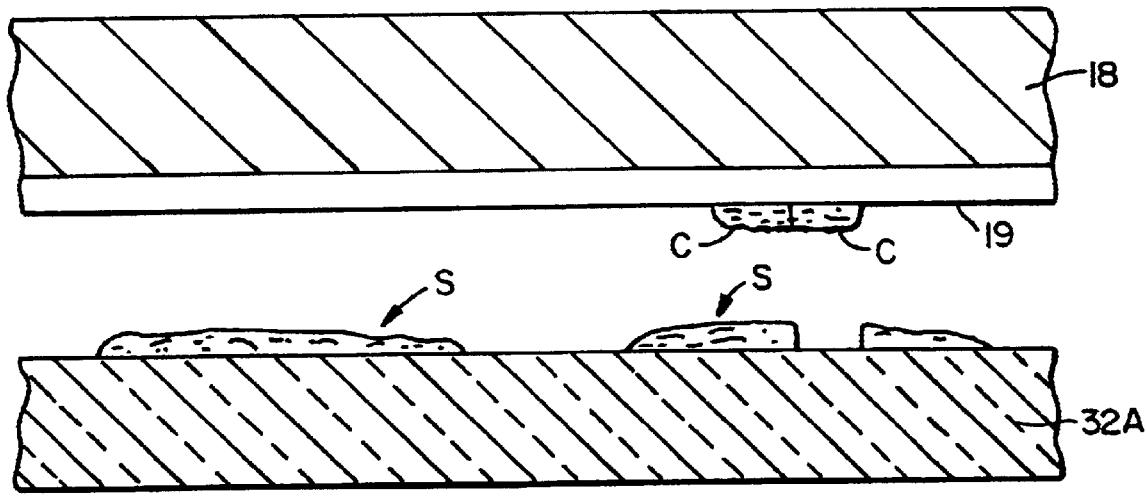

Referring to FIG. 14D, several additional advantages of this system can be seen. First, coated tape 18 can be transported so that a new segment of the coated tape overlies a targeted portion of a sample S on slide 32. Second, a new slide 32A can be introduced; thus several differing samples S from differing slides can be utilized for the collection and concentration of selected cellular material C. Thus, and referring to FIG. 14E, it will be seen that tissue from two slides 32 and 32A ends up side-by-side on coated tape 18.

Finally, the collection here illustrated amounts to a concentration of material not found on the original samples. This is particularly important where the sought after selected cellular material is originally scattered in situ or heterogeneous dispersed but needs to be concentrated above a certain threshold quantity to be meaningfully analyzed.

We use the term "apposition" in the following claims. This term is utilized to cover both contact and non-contact of the transporting substrate to the selected portion of the sample. Specifically, and where "apposition" is used, it will be understood that the substrate is close enough to the sample so that upon activation a bond to the selected cellular material can be formed.

What is claimed is:

1. In a method of designating location of selected and identified cellular material gathered on a transporting substrate from a tissue sample which comprises the steps of:

providing a transporting substrate;

providing a mapped location on the transporting substrate;

placing at least a segment of selectively activated coating on one side of the transporting substrate at the mapped location on the transporting substrate, the segment of selectively activated coating becoming adhesive to the tissue sample upon activation;

moving the transporting substrate to place the selectively activated coating at the mapped location in apposition to identified cellular material of the tissue sample which is to be extracted;

impressing the transporting substrate toward the tissue sample to bring the selectively activated coating in contact with the identified cellular material of the tissue sample, the impressing occurring through a device from the group consisting of a strut arrays a linear spoke array, and a circular spoke array;

selectively activating the selectively activated coating to form an adhesive region on the transporting substrate for adhering to the identified cellular material; and, removing the transporting substrate with the identified cellular material of the tissue sample being attached to the adhesive region whereby the identified cellular material from the tissue sample is at the mapped location on the transporting substrate.

2. A method of designating location of selected and identified cellular material according to claim 1 and wherein the impressing step includes:

providing a wheel with struts; and, applying pressure on the transporting substrate through an individually selected strut to impress the selectively activated coating onto the identified cellular material.

3. A method of designating location of selected and identified cellular material according to claim 1 and wherein the impressing step includes:

providing a plurality of struts linearly arrayed; and, applying pressure on the transporting substrate through a selected individual strut to impress the selectively activated coating onto the identified cellular material.

4. In a method designating location of selected and identified cellular material gathered on a transporting substrate from a tissue sample which comprises the steps of:

observing a tissue sample in a microscope to precisely locate identified cellular material relative to a microscope field for dissection from the tissue sample;

providing a transporting substrate;

providing a mapped location on the transporting substrate;

placing at least a segment of selectively activated coating on one side of the transporting substrate at the mapped location, the segment of selectively activated coating forming an adhesive region for the tissue sample upon activation;

transporting the selectively activated coating on the transporting substrate into apposition with identified cellular material of the tissue sample which is to be extracted but with a small spatial separation between the transporting substrate and tissue;

selectively activating the selectively activated coating to cause activated portions of the selectively activated coating to extend across the small spatial separation and come into contact with the identified cellular material of the tissue sample to form an adhesive region on the transporting substrate in contact with the identified cellular material; and, removing the transporting substrate with the identified cellular material of the tissue sample being attached to the adhesive region whereby the identified cellular material is attached to the transporting substrate at the mapped location.

5. In a method designating location of selected and identified cellular material gathered on a transporting substrate from a tissue sample according to claim 4 which comprises the further steps of:

placing at least one spacer between the selectively activated coating and the identified cellular material to maintain their apposition with the small spatial separation.

6. Apparatus for collecting identified cellular material from a tissue sample comprising:

a transporting substrate;

a mapped location on the transporting substrate;

at least a segment of selectively activated coating on one side of the transporting substrate at the mapped location on the transporting substrate, the segment of selectively activated coating becoming adhesive to the tissue sample upon activation;

means for moving the transporting substrate to place the selectively activated coating at the mapped location in apposition to identified cellular material of the tissue sample which is to be extracted;

means for impressing the transporting substrate toward the tissue sample to bring the selectively activated coating in contact with the identified cellular material of the tissue sample, the means for impressing selected from the group consisting of a spoke array, a linear spoke array and a circular spoke array;

means for activating the selectively activated coating to form an adhesive region on the transporting substrate for adhering to the identified cellular material; and, means for removing the transporting substrate with the identified cellular material of the tissue sample being attached to the adhesive region whereby the identified cellular material from the tissue sample is at the mapped location on the transporting substrate.

7. Apparatus for collecting identified cellular material from a tissue sample according to claim 6 wherein the means for impressing includes:

a wheel with spokes; and, means for applying pressure on the transporting substrate through each individual selected spoke to impress the selectively activated coating onto the identified cellular material.

8. Apparatus for collecting identified cellular material from a tissue sample according to claim 6 wherein the means for impressing includes:

a plurality of fingers linearly arrayed; and, means for applying pressure on the transporting substrate through each individual selected finger to impress the selectively activated coating onto the identified cellular material.

9. Apparatus for placing selected and identified cellular material on a transporting substrate from a tissue sample comprising:

means to precisely locate identified cellular material relative to a microscope field for dissection from the tissue sample;

a transporting substrate;

a mapped location on the transporting substrate;

at least a segment of selectively activated coating on one side of the transporting substrate at the mapped location, the segment of selectively activated coating having an adhesive region to the tissue sample upon activation;

means for transporting the selectively activated coating on the transporting substrate into apposition with identified cellular material of the tissue sample which is to be extracted;

means arranged to hold the transporting substrate at the selectively activated coating with a small spatial separation from the identified cellular material;

means for activating the selectively activated coating to cause activated portions of the selectively activated coating to extend across the small spatial separation and come into contact with the identified cellular material of the tissue sample to form an adhesive region on the transporting substrate in contact with the identified cellular material; and, means for removing the transporting substrate with the identified cellular material of the tissue sample being attached to the adhesive region whereby the identified cellular material is attached to the transporting substrate at the mapped location.

10. Apparatus for placing selected and identified cellular material on a transporting substrate from a tissue sample according to claim 9 and further comprising:

placing at least one spacer between the selectively activated coating and the cellular material to maintain apposition with the small spatial separation.

* * * * *